United States Patent [19]

Uchida et al.

[11] Patent Number: 5,294,554
[45] Date of Patent: Mar. 15, 1994

[54] ANALYSIS OF TIN, LEAD OR TIN-LEAD ALLOY PLATING SOLUTION

[75] Inventors: Hiroki Uchida; Motonobu Kubo; Masayuki Kiso; Teruyuki Hotta; Tohru Kamitamari, all of Hirakata, Japan

[73] Assignee: C. Uyemura & Co., Ltd., Osaka, Japan

[21] Appl. No.: 843,199

[22] Filed: Feb. 28, 1992

[30] Foreign Application Priority Data

| Mar. 1, 1991 | [JP] | Japan | 3-59643 |
| Nov. 11, 1991 | [JP] | Japan | 3-322535 |
| Nov. 11, 1991 | [JP] | Japan | 3-322536 |
| Nov. 11, 1991 | [JP] | Japan | 3-322537 |

[51] Int. Cl.$^5$ .......................... G01N 33/20
[52] U.S. Cl. ..................... 436/73; 436/77; 436/80; 422/68.1; 422/78
[58] Field of Search ........... 436/73, 77, 80, 166, 436/164, 177; 422/68.1, 78

[56] References Cited

U.S. PATENT DOCUMENTS

| 3,955,927 | 5/1976 | Zelaskowski et al. | 436/77 |
| 3,992,149 | 11/1976 | Wang | 436/164 |
| 4,684,404 | 8/1987 | Kalocsai | 436/26 |
| 5,057,302 | 10/1991 | Johnson et al. | 436/504 |

FOREIGN PATENT DOCUMENTS

| 0070889 | 6/1977 | Japan | 436/73 |
| 0086755 | 5/1982 | Japan | 436/73 |
| 0033045 | 2/1985 | Japan | 436/77 |
| 1090059 | 5/1986 | Japan | 436/164 |
| 1557494 | 4/1990 | U.S.S.R. | 436/80 |

OTHER PUBLICATIONS

Hwang and Linda Sandonato, Rapid Determinations of the Trace and Minor Elements in Tin-Lead Solders by Atomic Absorption Spectrometry, Jun. 1970, Analytical Chemistry, vol. 42, No. 7.
Database WPIL & Su-A-1 503 008.
Database WPIL & JP-A-02 201 264.
Database Analytical Abstracts & Diandu Yu Huanbao, vol. 10, No. 1.
Chemical Abstracts, vol. 114, No. 10.
Database Analytical Abstracts & ZH. Anal. Khim., vol. 41, No. 6.
Database Analytical Abstracts & Analyst, vol. 112, No. 3.

*Primary Examiner*—James C. Housel
*Assistant Examiner*—Harold Y. Pyon
*Attorney, Agent, or Firm*—Birch, Stewart, Kolasch & Birch

[57] ABSTRACT

In electroless or electric tin, lead or tin-lead alloy plating solution which may contain copper, the concentration of a metal ion component selected from divalent tin ion, lead ion, and copper ion is quantitatively determined by taking a sample from the solution, adding a chemical agent, for example, an oxidizing agent to the sample, thereby causing the selected metal ion to develop its color, measuring the absorbance of the sample due to the metal ion by colorimetry, and determining the concentration from the absorbance. A choice of chemical agent depends on a particular metal ion on analysis. When the solution contains more than one metal ion, correction is made by repeating the process using another chemical agent.

25 Claims, No Drawings

ANALYSIS OF TIN, LEAD OR TIN-LEAD ALLOY PLATING SOLUTION

This invention relates to a method for analysis of tin, lead or tin-lead alloy plating solution, and more particularly, to a simple and accurate method for quantitatively determining the concentrations of divalent tin ion, lead ion, and contaminating copper ion by colorimetry.

BACKGROUND OF THE INVENTION

In the electronic industry, for imparting solder receptivity to copper or copper alloy portions on electronic parts and circuits, it has been a common practice to form a tin, lead or tin-lead alloy (i.e., solder) coating on the copper or copper alloy portions by electroplating techniques As electronic devices are reduced in size, parts and circuits are also miniaturized or complicated. Some finely defined portions are difficult to plate by electroplating techniques. Of interest are electroless or chemical tin, lead or tin-lead plating techniques capable of plating on such finely defined portions.

Among electroless plating techniques for imparting solder receptivity, electroless tin plating has been used in practice. Electroless tin plating is generally intended for depositing thin films and uses a batchwise bath which is discharged without replenishment. In the case of electroless tin-lead alloy plating intended for depositing thick films, or if electroless tin or lead plating is intended for depositing thick films, it is necessary to maintain a constant rate of deposition. This necessitates replenishing chemical reagents as they are consumed.

Chemical reagents are generally replenished to the plating solution by analyzing the plating solution to measure the concentration of metal ion, calculating the amount of metal ion consumed (loss), and making up the reagent in an amount corresponding to the loss.

For assuring a constant rate of deposition, continuous replenishment of chemical reagents is necessary, which necessitates automatic monitoring of the concentration of relevant metal ion in the solution. However, lead and tin contained in tin, lead or tin-lead alloy plating baths are elements which are difficult to quantitatively analyze. Although several methods are known for measuring these elements, these methods have several problems. An analytical method which is accurate and adapted for automatic determination has not been available.

Analysis of lead ion is carried out by chelate titration using EDTA, precipitation of $PbSO_4$ followed by measurement of the precipitate weight, or the like. The chelate titration technique suffers from low accuracy because it is very difficult to judge the end of titration The weight analysis technique requires cumbersome steps of filtration and drying and cannot be automated.

Analysis of tin ion is by reducing a tetravalent tin ion in a plating solution to a divalent tin ion and titrating the divalent tin ion with iodine or by chelate titration of a plating solution approximately at pH 5 using EDTA. The iodometric titration technique is not applicable to plating solutions containing another reducing compound. The chelate titration technique suffers from the same problems as above.

These analytical methods are difficult to apply to the bath management of tin, lead or tin-lead alloy plating solutions. There is a need for an analytical method which allows for accurate analysis of tin, lead or tin-lead alloy plating solutions for easy and consistent management thereof.

SUMMARY OF THE INVENTION

Therefore, a primary object of the present invention is to provide an analytical method which ensures simple and accurate quantitative determination of metal ions in tin, lead or tin-lead alloy plating solutions and which can be utilized for management of the plating solutions.

The inventors investigated how to analyze the concentration of metal ions in a tin, lead or tin-lead alloy plating bath. Regarding electroless plating of tin, lead or tin-lead alloy on copper or copper alloy conductors, we have found that copper is dissolved into the bath from the copper or copper alloy which constitutes an article to be plated and at the same time, tin, lead or tin-lead alloy is deposited on the article to form a coating thereon. Namely, copper builds up in the plating bath with the progress of plating. The amount of copper ion dissolved into the plating bath is in proportion to the amount of tin and/or lead consumed. Then, by analyzing the concentration of copper ion dissolved in the plating bath and replenishing a water soluble tin and/or lead salt in response to the analyzed copper ion concentration, the electroless tin, lead or tin-lead alloy plating bath is controllable in a simple and consistent manner.

To establish a simple and accurate method capable of analyzing the concentration of copper ion dissolved in such electroless plating bath, we were interested in colorimetry because of easy automation and simple concentration measurement. We have found that the concentration of copper ion in an electroless tin, lead or tin-lead alloy plating solution can be accurately analyzed by taking a sample from the solution, adding an oxidizing agent to the sample, thereby oxidizing a monovalent copper ion in the sample to a divalent copper ion, causing the divalent copper ion to develop its color with the aid of a color developing agent, and quantitatively determining the concentration of divalent copper ion by colorimetry, typically absorbance measurement.

An electroless plating bath for plating on copper or copper alloy conductors usually contains a water soluble tin and/or lead salt, an acid capable of dissolving the acids, and thiourea complexing agent It is desired to analyze the concentration of copper ion dissolving into the bath. Quantitative determination of the copper ion concentration in the bath can be accurately and simply made by first effecting oxidative decomposition of thiourea in the bath, oxidizing a monovalent copper ion into a divalent copper ion, and analyzing the total concentration of divalent copper ions including oxidized ones by colorimetry.

More particularly, in electroless tin, lead or tin-lead alloy plating, copper is dissolved out from an article to be plated and builds up in the bath with the progress of plating. Our study of the bath shows that copper forms a complex with thiourea in the bath and that part of the copper is present as divalent copper ions, but the majority are present as monovalent copper ions As to the concentration of copper ion in such a state, the total amount of copper can be quantitatively determined by atomic absorption spectroscopy. In an attempt to utilize a colorimetric technique which is advantageous to perform in plating facilities, we found that the bath was not liable to colorimetric analysis without any treatment. Continuing study, we have found that the total quantity of copper ion can be accurately determined if colorimetric analysis is carried out after an oxidizing agent capable of decomposing thiourea such as hydrogen peroxide and perchlorates is added to the solution for decomposing thiourea and additionally, oxidizing a monovalent copper ion into a divalent copper ion. The thus determined total quantity of copper ion provides a measure on the basis of which a tin or lead salt is replenished to the bath.

In addition to the first-mentioned analytical method, we also investigated how to determine the concentration of lead ion and divalent tin ion in a tin, lead or tin-lead alloy plating solution by colorimetry using absorbance measurement adapted for automatic analysis We have found that the concentration of lead ion can be measured by adding an iodide followed by absorbance measurement and that the concentration of divalent tin ion can be accurately determined by adding thiourea or its derivative to the solution, carrying out absorbance measurement on the solution for obtaining the combined absorbance of lead ion and divalent tin ion, subtracting the absorbance of lead ion measured above from the combined absorbance, thereby calculating a net absorbance attributable to only divalent tin ion, and calculating the concentration of divalent tin ion from the net absorbance.

In a further attempt to measure the concentrations of lead ion and divalent tin ion in an electroless tin, lead or tin-lead alloy plating bath intended for plating on copper or copper alloy conductors, using the above method, we failed to obtain accurate measurements. Studying the cause, we have found that when electroless plating of tin, lead or tin-lead alloy is carried out on copper or copper alloy members, copper ions are dissolved from the members into the bath and build up in the bath where the majority of copper ions are present as monovalent copper ions. These monovalent copper ions are detectable at the same time as the above-mentioned measurement of lead ion concentration by absorbance measurement assisted by the addition of an iodide. The absorbance measured at this point is a combined absorbance of lead and copper ions. That is, the absorbance component assigned to copper ion becomes a factor of disturbing the quantitative determination of lead and tin ions.

We continued further investigation on how to correct a measurement error introduced by copper ion We have found that lead ion concentration determination by absorbance measurement can be corrected by measuring a copper ion concentration in the plating solution by the first-mentioned analytical method, measuring the lead ion concentration through measurement of an apparent absorbance of the solution as mentioned above, calculating an absorbance component assigned to copper ion from the copper ion concentration measurement, subtracting this absorbance component from the apparent absorbance, thereby calculating a net absorbance assigned to lead ion, and calculating an accurate lead ion concentration from the net absorbance. Subsequently, tin ion concentration determination by absorbance measurement can be corrected by calculating an absorbance component assigned to lead ion from the above-calculated lead ion concentration, subtracting this absorbance component from the combined absorbance of lead and tin ions, thereby calculating a net absorbance assigned to tin ion, and calculating an accurate tin ion concentration from the net absorbance.

Accordingly, the present invention provides several forms of analysis of tin, lead or tin-lead alloy plating solution.

One form of the present invention provides a method for analyzing a tin, lead or tin-lead alloy plating solution having copper dissolved therein, comprising the steps of: taking a sample from the solution, adding an oxidizing agent to the sample, thereby oxidizing a monovalent copper ion in the sample to a divalent copper ion, and quantitatively determining the concentration of divalent copper ion by colorimetry. When copper is present as a complex with thiourea or its derivative in the plating solution, the step of adding an oxidizing agent to the sample induces U simultaneously decomposition of the thiourea or its derivative and oxidation of monovalent copper ion to divalent copper ion.

Another form of the present invention provides a method for analyzing a tin, lead or tin-lead alloy plating solution containing at least one divalent metal ion selected from the group consisting of tin and lead ions, comprising the steps of: taking a sample from the solution, adding thiourea or its derivative to the sample, thereby causing the divalent metal ion to develop its color, and quantitatively determining the concentration of the divalent metal ion by colorimetry.

Further form of the present invention provides a method for analyzing a lead or tin-lead alloy plating solution which may contain a copper ion in addition to a lead ion, comprising the steps of:

taking a sample from the solution,
adding an iodide to the sample, causing the lead ion and optional copper ion to develop their color, and
quantitatively determining the (combined) concentration of lead ion and optional copper ion by colorimetry, and
if the copper ion is contained, subtracting the concentration of copper ion from the combined concentration for providing a quantitative determination of lead ion Still further form of the present invention provides a method for analyzing a tin-lead alloy plating solution optionally containing a copper ion for quantitative determination of divalent tin ion and lead ion, the method comprising the steps of:

taking a sample from the solution,
adding an iodide to the sample, causing the lead ion and optional copper ion to develop their color,
quantitatively determining the (combined) concentration of lead ion and optional copper ion by colorimetry,
if copper ion is contained, subtracting the concentration of copper ion from the combined concentration of lead and copper ions for providing a quantitative determination of lead ion;
taking another sample from the solution,
adding thiourea or its derivative to the other sample, causing the divalent tin ion and lead ion to develop their color,
quantitatively determining the combined concentration of divalent tin and lead ions by colorimetry,
subtracting the concentration of lead ion from the combined concentration of divalent tin ion and lead ion for providing a quantitative determination of divalent tin ion.

Yet further form of the present invention provides a method for analyzing an electroless tin-lead alloy plating solution for quantitative determination of copper ion, lead ion, and divalent tin ion, comprising the steps of:

(1) taking a first sample from the solution, adding an oxidizing agent to the first sample, thereby converting a monovalent copper ion to a divalent copper ion, and determining the concentration of copper ion by colorimetry, (2) taking a second sample from the solution, adding an iodide to the second sample, measuring the absorbance of the second sample for providing a combined absorbance of copper and lead ions, subtracting an absorbance attributable to copper ion as calculated from the concentration of copper ion determined in (1) from the combined absorbance for providing an absorbance attributable to only lead ion, and calculating the concentration of lead ion from the absorbance of lead ion, and (3) taking a third sample from the solution, adding thiourea or its derivative to the third sample, measuring the absorbance of the third sample for providing a combined absorbance of divalent tin and lead ions, subtracting an absorbance attributable to lead ion as calculated from the concentration of lead ion determined in (2) from the combined absorbance for providing an absorbance attributable to only divalent tin ion, and calculating the concentration of divalent tin ion from the absorbance of divalent tin ion.

DETAILED DESCRIPTION OF THE INVENTION

According to the first form of analytical method of the present invention, a tin, lead or tin-lead alloy plating solution having copper dissolved therein is analyzed for copper content by taking a sample from the solution, adding an oxidizing agent to the sample, thereby oxidizing a monovalent copper ion in the sample to a divalent copper ion, and quantitatively determining the concentration of divalent copper ion by colorimetry.

The first form of analytical method of the present invention is intended to analyze electroless tin, lead or tin-lead alloy plating baths which generally contain as main ingredients a metal salt component selected from the group consisting of a water soluble tin salt, a water soluble lead salt and a mixture thereof, an acid component capable of dissolving the metal salt component, and a complexing agent.

Examples of the water soluble tin salt include stannous chloride, stannous sulfate, stannous alkane sulfonates, stannous alkanol sulfonates, and stannous sulfosuccinate, Examples of the water soluble lead salt include lead chloride, lead acetate, lead alkane sulfonates, and lead alkanol sulfonates. These metal salt components are preferably contained in amounts of about 0.5 to 50 grams/liter, especially about 1 to 30 grams/liter. The acid component capable of dissolving these metal salts includes hydrochloric acid, perchloric acid, fluoroboric acid, alkane sulfonic acids, alkanol sulfonic acids, and sulfosuccinic acid. The acids are preferably used in amounts of about 10 to 250 grams/liter, especially about 50 to 200 grams/liter. The complexing agent includes organic acids such as citric acid, amines such as ethylenediaminetetraacetic acid (EDTA), thiourea, and thiourea derivatives. Preferred complexing agents are thiourea and its derivatives, for example, thioamides such as thioformamide and thioacetamide. The complexing agents are preferably used in amounts of about 10 to 200 grams/liter, especially about 30 to 100 grams/liter.

To the electroless plating bath is generally added a reducing agent, for example, hypophosphorous acid and water soluble hypophosphites, in amounts of from about 10 to 300 grams/liter, preferably from about 10 to 200 grams/liter. The plating bath is generally at pH 0 to 3, especially pH 0.5 to 2 5.

Chemical plating process using the above-defined plating bath is by dipping an article to be plated at least a portion of which is formed of copper or copper alloy in the bath, thereby depositing a coating of tin, lead or tin-lead alloy on the copper or copper alloy portion of the article. During the process, copper ion is dissolved from the article and builds up in the bath simultaneously with deposition of tin, lead or tin-lead alloy.

The first form of analytical method of the invention is to quantitatively determine the concentration of copper ion in the bath. In the bath, the copper ion forms a complex with thiourea and the majority thereof are present as monovalent copper ions This coincides with the fact that the bath is generally colorless According to the first form of analytical method of the invention, the concentration of overall copper ions is measured by first adding an oxidizing agent to the solution, typically a sample taken from the plating bath on analysis, thereby causing oxidative decomposition of the thiourea or its derivative to cancel complex formation between copper ion and thiourea and to oxidize monovalent copper ions to divalent copper ions.

Any oxidizing agent which is colorless, capable of decomposing thiourea, and not colored through oxidation reaction may be used. Preferred oxidizing agents are peroxides such as hydrogen peroxide and persulfates, chlorous acid and chlorites, with the hydrogen peroxide being most preferred. The oxidizing agent is added in an amount capable of decomposing thiourea and oxidizing monovalent copper ions to divalent copper ions. For example, about 0.1 to 2 grams of aqueous hydrogen peroxide is added to 1 ml of the plating solution.

At the same time as thiourea is decomposed by the addition of the oxidizing agent, the metal ions which have formed complexes with thiourea, that is, tin ions (especially $Sn^{4+}$) and lead ions are liberated and can precipitate to render the plating solution white turbid For preventing such precipitation, there may be added a complexing agent capable of forming complexes with $Sn^{4+}$ and $Pb^{2+}$, for example, oxalic acid, tartaric acid, citric acid, EDTA and its salts, and triethanol amine. About 1 to 100 grams of the complexing agent is generally added to 1 ml of the plating solution.

Since the addition of an oxidizing agent induces oxidation of a colorless monovalent copper ion to a normally blue divalent copper ion so that the plating solution is colored blue, the final step of the analytical method is to quantitatively determine the color of the plating solution by colorimetry. A color developing agent may be added to ensure that the solution is colored with divalent copper ions, differently stated, to increase the divalent copper ion detection sensitivity. Examples of the color developing agent include ammonia and amines such as ethylenediamine, diethylenetriamine, triethylenetriamine, tetraethylene-pentamine, and aminoethylmonoethanolamine. About 0.2 to 5 grams of the color developing agent is generally added to 1 ml of the plating solution Exemplary of the other useful color developing agents are 2,2'-bipyridyl, 1,10- phenanthroline, and phenanthroline derivatives such as bathophenanthroline, cuproine, neocuproine, and bathocuproine.

If a solution sample on analysis is below pH 4, especially below pH 1, the divalent copper ion can not develop its color to a full extent. In excess of pH 11, the oxidizing agent, e.g., hydrogen peroxide can decompose to create bubbles which would affect the absorbance of the sample. For these reasons, the solution sample is preferably at pH 1-11, especially at pH 4-11. Since the permissible pH range is as wide as from 4 to 11, a special pH adjusting agent or buffer agent is necessary only in a few cases. If pH adjustment is necessary, acetic acid, acetates, hexaethylenetetramine and other buffer agents at pH 4.11 may be used. The colored sample may be measured for absorbance directly or after dilution.

The order of adding the oxidizing agent, complexing agent, color developing agent, and pH adjusting agent is not critical. Although these agents can be added all at once, one preferred procedure involves first addition of the complexing agent, pH adjustment, addition of the oxidizing agent, and final addition of the color developing agent.

The sample which is colored as a result of decomposition of thiourea or its derivative and oxidation of monovalent copper ion into divalent copper ion is then quantitatively determined by colorimetry. The colorimetry may be a primitive method of visually comparing a sample with a reference sample, although it is often recommended to measure the absorbance of a sample at a wavelength of 500 to 800 nm and compare the measurement with a calibration chart previously obtained from reference samples. The wavelength at which absorbance measurement is done may be suitably chosen in accordance with the color developing agent if it is used. For example, wavelengths of nearly 740 nm and 710 nm are used for 2,2'-bipyridyl and 1,10-phenanthroline color developing agents, respectively.

Analysis may be conducted in various modes One mode involves taking aliquots from the plating bath at suitable intervals and repeating the above mentioned analysis steps for each aliquot In an alternative mode, a test solution is continuously pumped from the plating bath to an 0 analytical equipment where the solution is automatically pretreated by the above-mentioned procedure and passed to a flow cell for continuously measuring absorbance.

The copper ion concentration is quantitatively determined in this way and is useful in the management of an electroless tin, lead or tin-lead alloy plating bath for controlling its tin and lead contents. More particularly, since the copper ion concentration in the bath is in proportion to the amount of metal (tin and lead) consumed, the copper ion concentration can be used as a measure on the basis of which the metal components are replenished to the bath. By replenishing tin and lead salts to the bath in proportion to an increase of the copper ion concentration, the tin and lead contents in the bath can be controlled to an optimum level.

In this way, the analytical method according to the first form of the invention can readily and accurately analyze the copper ion concentration of an electroless tin, lead or tin-lead alloy plating solution. Since the analytical step is based on colorimetry which is adapted for automatic analysis, the method can be advantageously utilized in the management of electroless tin, lead or tin-lead alloy plating solution.

The second form of analytical method of the present invention is a method for quantitative determination of the quantity of divalent tin ion or lead ion or the combined quantity of divalent tin ion and lead ion in a tin, lead or tin-lead alloy plating solution The method involves the steps of taking a sample from the solution, adding thiourea or its derivative to the sample, thereby causing the divalent tin ion and lead ion to develop their color, and quantitatively determining the concentration of divalent tin ion or lead ion or the combined concentration of divalent tin ion and lead ion by colorimetry.

The second form of analytical method of the present invention is intended to analyze plating solutions containing a divalent tin ion and/or a lead ion. Both electric and electroless plating solutions are included. Typical electroplating solutions are tin, lead or tin-lead alloy electroplating baths, for example, sulfuric acid and fluoroboric acid base baths containing a water soluble stannous salt and/or lead salt, and alkaline baths containing stannates such as potassium stannate and sodium stannate. Typical electroless plating solutions are electroless tin or tin-lead alloy plating baths containing a water soluble stannous salt and/or lead salt, an acid capable of dissolving the salts, a complexing agent, and a reducing agent.

According to the second form of analytical method of the present invention, thiourea or its derivative is added to an aliquot sampled from the plating solution, thereby causing the divalent tin ion and lead ion to develop their color, and the colored aliquot is measured for absorbance. Examples of the thiourea derivative include dimethyl-thiourea, diethylthiourea, dimethylolthiourea, and diphenyl-thiourea. Thiourea or its derivative is preferably added in an amount of about 1 to 100 grams, more preferably about 5 to 100 grams, most preferably about 5 to 20 grams per milliliter (ml) of the plating solution. The sample solution should be acidic, preferably at pH 0 to 5. Hydrochloric acid or the like may be used for pH adjustment.

The thus adjusted sample is diluted if desired and measured for absorbance. That is, the absorbance of divalent tin ion and/or lead ion is measured Although the measurement wavelength is not critical, a wavelength of nearly 370 nm is preferred for analysis accuracy At a wavelength far apart from 370 nm, the absorbance of other elements, typically copper ion dissolving out of articles to be plated in the case of electroless plating, can also be detected, leading to a lowering of analysis accuracy.

In the quantitative determination of tin ion according to the second form of analytical method of the invention, the detectable tin ion is only a divalent one. However, since the majority of tin ions in plating solution are divalent tin ions, the analytical method of the invention is applicable to the management of plating bath without any problem in practice. If a substantial amount of tetravalent tin ion is contained or if it is necessary to determine a more accurate amount of tin, a reducing agent is added to the sample for converting the tetravalent tin ions into divalent tin ions. The reducing agents used for such purposes include metallic Zn powder, tetrahydroborates, hydrazine and hydrazine salts.

In the case of a tin-lead alloy plating bath containing both tin ions and lead ions, the second form of analytical method of the invention measures the combined absorbance of tin and lead ions. In this case, the concentration of lead or tin ion alone is separately measured by the third form of analytical method of the invention or conventional iodometric titration, chelate titration or other techniques. An absorbance component attributable to lead or tin ion is calculated from the separately measured concentration of lead or tin ion and subtracted from the combined absorbance, obtaining an absorbance component attributable to tin or lead ion alone. From this absorbance, the concentration of tin or lead ion is calculated.

The second form of analytical method of the invention is advantageous over the prior art because of ease of operation or the like even when the concentration of either lead or tin ion must be measured by a conventional technique. For example, the quantity of lead ion in a tin-lead alloy plating bath is determined according to the invention by quantitatively determining the concentration of tin ion by iodometric titration, calculating an absorbance component of tin ion, and subtracting this absorbance component from the combined absorbance of tin and lead ions for obtaining an absorbance component of lead ion, and calculating the lead ion concentration therefrom. This method can readily accomplish quantitative determination of lead ion, as compared with the prior art method for determining the lead ion concentration by weight analysis which requires filtration and drying steps.

It will be appreciated that the concentration of divalent tin ion or lead ion or the combined concentration of divalent tin ion and lead ion is obtained from an absorbance measurement preferably by comparing the measurement with a calibration chart previously obtained from standard samples. The absorbance measurement may be carried out in various modes. Modes adapted for automatic determination are preferred, one mode involving sampling aliquots from the plating bath at intervals, treating each aliquot, and passing the colored aliquot through an absorptiometric cell Alternatively, a sample solution flow is continuously taken out of the plating bath, mixed with thiourea, and passed through an absorptiometric cell whereby absorbance is continuously measured.

The third form of analytical method of the present invention is to determine the quantity of lead ion in a lead or tin-lead alloy plating solution by taking a sample from the solution, adding an iodide to the sample for causing the lead ion to develop its color, and quantitatively determining the concentration of lead ion by colorimetry. When the lead or tin-lead alloy plating solution containing a copper ion in addition to a lead ion, the method is modified as comprising the steps of adding an iodide to the sample for causing the lead and copper ions to develop their color, quantitatively determining the combined concentration of lead and copper ions by colorimetry, and subtracting the concentration of copper ion from the combined concentration for providing a quantitative determination of lead ion.

The third form of analytical method of the invention is intended to analyze lead or lead alloy electroplating baths containing a water soluble lead salt and an acid capable of dissolving the salt, but substantially free of a copper ion. Often, lead or lead alloy electroplating baths contain a lead salt such as lead chloride, lead acetate, lead alkane sulfonates, and lead alkanol sulfonates in an amount of about 0.1 to 50 grams/liter of Pb, and an acid such as hydrochloric acid, perchloric acid, fluoroboric acid, alkane sulfonic acids, alkanol sulfonic acids, and sulfosuccinic acid in an amount of about 10 to 200 grams/liter. Typical of the lead alloy electroplating bath is a tin-lead alloy (solder) electroplating bath.

Also, an electroless tin-lead alloy plating solution having a copper ion dissolved therein can be analyzed by the third form of analytical method of the invention.

The iodides used herein include KI and NaI, for example. About 0.1 to 50 grams, especially about 0.5 to 10 grams of the iodide is added to 1 ml of the plating solution. Since the addition of an iodide to the plating solution is sometimes accompanied by precipitation, a complexing agent is preferably added for preventing precipitation. Exemplary of the complexing agent are oxalic acid, tartaric acid, citric acid, EDTA, hydroxyphosphoric acid and salts thereof. About 1 to 100 grams, especially about 1 to 10 grams of the complexing agent is added to 1 ml of the plating solution. The sample solution should preferably be at pH 0 to 5.

The thus adjusted sample is diluted if desired and measured for absorbance. That is, the absorbance of lead ion is measured Although the measurement wavelength is not critical, a wavelength of nearly 340 nm is preferred for analysis accuracy At a wavelength far apart from 340 nm, the absorbance of tin and other ions can also be detected, leading to a lowering of analysis accuracy.

In the case of a plating solution or sample containing a copper ion (especially monovalent copper ion) in addition to a lead ion, the third form of analytical method of the invention measures the combined concentration of lead and copper ions. Then the concentration of copper ion is separately measured by any desired method, preferably by the first form of analytical method of the invention. The combined concentration minus the copper ion concentration provides a net concentration of lead ion. More particularly, after the combined absorbance of lead and copper ions is obtained, the absorbance of copper ion is separately measured by the first form of analytical method of the invention and subtracted from the combined absorbance, obtaining an absorbance component attributable to only lead ion. From this absorbance, the concentration of lead ion is calculated.

The fourth form of analytical method of the present invention is a combination of the second and third forms mentioned above. For quantitative determination of divalent tin ion and lead ion in a tin-lead alloy plating solution which may optionally contain a copper ion, the analytic method includes the steps of: taking a sample from the solution, adding an iodide to the sample for causing the lead ion to develop its color or the lead and copper ions to develop their color if copper is contained, quantitatively determining the concentration of lead ion or the combined concentration of lead and copper ions if copper is contained by colorimetry, and subtracting the concentration of copper ion from the combined concentration of lead and copper ions for providing a quantitative determination of lead ion. Next, divalent tin ion is quantitatively determined by taking another sample from the solution, adding thiourea or its derivative to the other sample for causing the divalent tin and lead ions to develop their color, quantitatively determining the combined concentration of divalent tin and lead ions by colorimetry, and subtracting the concentration of lead ion from the combined concentration of divalent tin and lead ions for providing the concentration of divalent tin ion.

Finally, the fifth form of analytical method of the present invention is a method for analyzing an electroless tin-lead alloy plating solution for quantitative determination of copper ion, lead ion, and divalent tin ion.

The fifth form is a combination of the first, second and third forms of analytical method mentioned above and adapted for the analysis of an electroless tin-lead alloy plating solution for plating on copper or copper alloy conductors.

(1) Copper ion is quantitatively determined by taking a first sample from the solution, adding an oxidizing agent to the first sample, thereby converting a monovalent copper ion to a divalent copper ion, and determining the concentration of copper ion by colorimetry. (2) Lead ion is quantitatively determined by taking a second sample from the solution, adding an iodide to the second sample, measuring the light absorbance of the second sample for providing a combined absorbance of copper and lead ions, subtracting an absorbance attributable to copper ion as calculated from the concentration of copper ion determined in (1) from the combined absorbance for providing an absorbance attributable to only lead ion, and calculating the concentration of lead ion from the absorbance of lead ion. (3) Divalent tin ion is quantitatively determined by taking a third sample from the solution, adding thiourea or its derivative to the third sample, measuring the absorbance of the third sample for providing a combined absorbance of divalent tin and lead ions, subtracting an absorbance attributable to lead ion as calculated from the concentration of lead ion determined in (2) from the combined absorbance for providing an absorbance attributable to only divalent tin ion, and calculating the concentration of divalent tin ion from the absorbance of divalent tin ion.

Procedure (1) for measuring the copper ion concentration is the same as the first form of analytical method of the invention.

Procedure (2) is in accord with the third form of analytical method of the invention. As previously mentioned, the absorbance of the second sample having an iodide added thereto is a combined absorbance of copper and lead ions. It is thus necessary to calculate an absorbance attributable to copper ion from the concentration of copper ion determined in (1) and subtract the copper ion absorbance from the combined absorbance for providing an absorbance attributable to only lead ion. The concentration of lead ion in the sample or electroless tin-lead alloy plating solution is then calculated from the lead ion absorbance. It is unknown whether the inhibiting copper ion is monovalent, divalent or a mixture of mono- and divalent ions. An absorbance component attributable to copper ion can be obtained by separately preparing a plating solution which contains copper ion in the same concentration as the copper ion concentration obtained by procedure (1), but is free of a lead ion, adding an iodide to the solution, and measuring the absorbance of the solution, thereby obtaining an absorbance component of copper ion. A net absorbance component of lead ion is then obtained therefrom.

Procedure (3) is in accord with the second form of analytical method of the invention. As previously mentioned, the absorbance of the third sample having thiourea or its derivative added thereto is a combined absorbance of divalent tin ion and lead ion. It is thus necessary to calculate an absorbance attributable to lead ion from the concentration of lead ion determined in (2) and to subtract the lead ion absorbance from the combined absorbance for providing an absorbance attributable to only divalent tin ion. The concentration of divalent tin ion in the sample or electroless tin, lead or tin-lead alloy plating solution is then calculated from the absorbance of divalent tin ion. An absorbance component attributable to lead ion can be obtained by separately preparing a plating solution which contains lead ion in the same concentration as the lead ion concentration obtained by procedure (2), but is free of a tin ion, adding thiourea or its derivative to the solution, and measuring the absorbance of the solution, thereby obtaining an absorbance component of lead ion. A net absorbance component of tin ion is then obtained therefrom.

In the respective metal ion concentration determining procedures (1) to (3) mentioned above, the respective metal ion concentrations can be determined from corresponding absorbance values by comparing them with calibration charts obtained from standard samples. Light absorbance may be measured by various techniques adapted for automatic measurement. One technique involves taking aliquots from the plating solution or bath at suitable intervals, processing each aliquot, and charging an absorptiometric cell with the colored aliquot. In an alternative technique, a test solution is continuously pumped from the plating bath, mixed with an analytical reagent, and then passed through an absorptiometric cell whereby continuous measurement is carried out.

The metal ion concentration determining method of the present invention can accurately measure the concentration of copper ion, lead ion, and divalent tin ion in plating solutions by utilizing a colorimetric technique which is adapted for automatic measurement. Therefore, the present method is advantageously employed for the control of plating solutions, especially chemical plating solutions. More particularly, the plating solution is managed by measuring the concentration of copper ion, lead ion, and divalent tin ion in the solution sequentially on every plating cycle or continuously in accordance with the analytical method of the invention, and making up a replenisher in a sequential replenishment mode or automatic drain mode using the measurement as an indicator.

EXAMPLE

Examples of the present invention are given below by way of illustration and not by way of limitation. It is noted that g/l is grams/liter. The colorimetric analysis used herein is by preparing several standard solutions having known metal concentrations, and subjecting the standard solutions to colorimetry, thereby determining a calibration curve representative of absorbance vs metal concentration. Thereafter, the metal concentration of each sample is determined by plotting an actual absorbance measurement of the sample on the calibration curve.

Example 1

There was prepared an electroless tin-lead alloy plating bath of the following composition where electroless plating was effected on copper articles under the following conditions. On every plating quantity of 26 $\mu m \cdot dm^2$/liter, a 5-ml aliquot was sampled from the bath. To each aliquot were added 200 ml of a solution containing 20 g/l of triethylenetriamine, 100 g/l of acetic acid, and 100 g/l of ammonium citrate and 2 ml of 35% aqueous hydrogen peroxide The absorbance of the sample was measured by means of a spectrophotometer Model U-3210 (manufactured by Hitachi, Ltd.) at a wavelength of 620 nm, determining the total quantity of copper. The results are shown in Table 1. For comparison purposes, the results of atomic absorption spectrometry (AAS) of the same aliquot are also reported in Table 1.

It is to be noted that whenever the copper concentration increased by 0.5 g/l with the progress of plating, the following replenishers (A) to (C) were supplied to the bath in the indicated rates.

| Bath composition and conditions | |
|---|---|
| Methanesulfonic acid | 50 g/l |
| Tin methanesulfonate | 20 g/l |
| Lead methanesulfonate | 13 g/l |
| Thiourea | 75 g/l |
| Sodium hypophosphite | 80 g/l |
| Citric acid | 15 g/l |
| Lauryl pyridinium chloride | 5 g/l |
| EDTA | 3 g/l |
| pH | 2.0 |
| Temperature | 80° C. |
| Replenisher (A): 5 ml/liter | |
| Tin methanesulfonate | 400 g/l |
| Methanesulfonic acid | 180 g/l |
| Replenisher (B): 5 ml/liter | |
| Lead methanesulfonate | 380 g/l |
| Methanesulfonic acid | 240 g/l |
| Replenisher (C): 15 ml/liter | |
| Thiourea | 120 g/l |
| Sodium hypophosphite | 3 g/l |
| Citric acid | 25 g/l |

TABLE 1

| Plating quantity | Analysis by the invention | Analysis by AAS |
|---|---|---|
| 26 μm · dm$^2$/l | 0.85 g/l | 0.89 g/l |
| 52 | 2.02 | 1.91 |
| 78 | 2.90 | 2.95 |
| 104 | 4.10 | 4.06 |
| 130 | 5.35 | 5.47 |
| 156 | 6.40 | 6.44 |
| 182 | 6.83 | 6.74 |

As is evident from Table 1, the analytical values of copper according to the method of the invention are substantially coincident with the analytical values by atomic absorption spectrometry. The method of the invention permits for easy and accurate determination of copper concentrations.

Example 2

Sequential replenishment system

Using a plating bath of the same composition as in Example 1, electroless plating was effected on copper articles under the same conditions as in Example 1. On every plating quantity of 10 μm·dm$^2$/liter, two aliquots were sampled from the bath and test samples, Nos. 2-1 and 2-2, were prepared therefrom. The test samples were measured for absorbance for determining the total quantity of copper The results are shown in Table 2. For comparison purposes, the results of atomic absorption spectrometry (AAS) of the same test samples are also reported in Table 2.

| Test sample No. 2-1 | |
|---|---|
| Plating solution | 1 ml |
| Tartaric acid (400 g/l) | 10 ml |
| 2,2′-bipyridyl | 0.2 g |
| 35% aqueous hydrogen peroxide | 2 ml |

It was diluted with deionized water to 50 ml and absorbance was measured at a wavelength of 740 nm.

| Test sample No. 2-2 | |
|---|---|
| Plating solution | 1 ml |
| Tartaric acid (400 g/l) | 10 ml |
| 1,10-phenanthroline | 0.2 g |
| 35% aqueous hydrogen peroxide | 2 ml |

It was diluted with deionized water to 50 ml and absorbance was measured at a wavelength of 710 nm.

TABLE 2

| Plating quantity | Analysis by the Invention | | Analysis by AAS |
|---|---|---|---|
| | No. 2-1 | No. 2-2 | |
| 20 μm · dm$^2$/l | 0.75 g/l | 0.80 g/l | 0.75 g/l |
| 40 | 1.60 | 1.65 | 1.55 |
| 60 | 2.35 | 2.40 | 2.45 |
| 80 | 3.30 | 3.20 | 3.15 |
| 100 | 4.10 | 4.15 | 4.00 |
| 120 | 4.80 | 4.95 | 4.90 |
| 140 | 5.75 | 5.70 | 5.80 |
| 160 | 6.60 | 6.45 | 6.65 |

As is evident from Table 2, the analytical values of copper according to the method of the invention are substantially coincident with the analytical values by atomic absorption spectrometry. The method of the invention permits for easy and accurate determination of copper concentrations.

Whenever the copper concentration as measured by the above-mentioned analytical method increased by 0 5 g/l with the progress of plating, replenishers (A) to (C) as used in Example 1 were supplied to the bath The concentrations of lead ion and divalent tin ion were determined by the following analytical methods for examining their change. The results are shown in Table 3. For comparison purposes, the respective metal ion concentration of the same samples as measured by atomic absorption spectrometry (AAS) are also reported in Table 3.

Analysis of lead ion

To a 1-ml aliquot sampled from the plating bath were added 10 ml of tartaric acid solution (400 g/l) and 10 ml of KI solution (100 g/l) It was diluted with deionized water to 100 ml. The sample solution in a cell was measured for absorbance at a wavelength of 340 nm to determine a combined absorbance of lead and copper ions. An absorbance component of copper was calculated from the copper ion concentration shown in Table 2. The combined absorbance minus the copper absorbance was a net absorbance of lead ion. A lead ion concentration was calculated from the lead absorbance.

Analysis of tin ion

To another 1-ml aliquot sampled from the plating bath were added 80 ml of thiourea solution (100 g/l) and 5 ml of aqueous HCl (1+1). It was diluted with deionized water to 100 ml. The sample solution in a cell was measured for absorbance at a wavelength of 340 nm to determine a combined absorbance of divalent tin ion plus lead ion. The combined absorbance minus the lead absorbance obtained above was a net absorbance of divalent tin ion. A divalent tin ion concentration was calculated from the tin absorbance.

TABLE 3

| Plating quantity | Analysis by Invention | | Analysis by AAS | |
| --- | --- | --- | --- | --- |
| | Pb ion | Sn ion | Pb ion | Sn ion |
| 13 μm·dm²/l | 6.80 g/l | 7.70 g/l | 6.80 g/l | 7.75 g/l |
| 25 | 6.85 | 7.65 | 6.80 | 7.70 |
| 37 | 6.75 | 7.70 | 6.70 | 7.75 |
| 49 | 6.80 | 7.65 | 6.75 | 7.60 |
| 61 | 6.75 | 7.75 | 6.80 | 7.75 |
| 73 | 6.80 | 7.75 | 6.85 | 7.80 |
| 86 | 6.90 | 7.70 | 6.85 | 7.75 |
| 98 | 6.85 | 7.65 | 6.90 | 7.75 |

As is evident from Table 3, the analytical values of lead and tin according to the method of the invention are substantially coincident with the analytical values by atomic absorption spectrometry. The method of the invention permits for easy and accurate determination of lead and tin concentrations.

Plating was continued by repeatedly dipping copper articles while the bath was managed by the above-mentioned procedure. Tin-lead alloy films of a fixed thickness consistently deposited on a number of copper articles while the bath maintained stable chemical deposition capability.

Example 3

Automatic drain system

Using an electroless tin-lead alloy plating bath of the same composition as in Example 1 except that 4.5 g/l of metallic copper was added on its preparation, electroless plating was effected on copper articles under the same conditions as in Example 1. The copper concentration was analyzed as in Example 2. Whenever the copper ion concentration reached 5.0 g/l, a 1/10 volume of the plating solution was discharged and the same volume of the following replenisher (D) was supplied to the bath. Deionized water was supplied to the bath until the desired surface level was reached. The concentrations of copper ion, lead ion and divalent tin ion were determined by the same analytical procedures as in Example 2 for examining their change.

| Replenisher (D) composition and conditions | |
| --- | --- |
| Methanesulfonic acid | 50 g/l |
| Tin methanesulfonate | 22 g/l |
| Lead methanesulfonate | 15 g/l |
| Thiourea | 83 g/l |
| Sodium hypophosphite | 80 g/l |
| Citric acid | 15 g/l |
| Lauryl pyridinium chloride | 5 g/l |
| EDTA | 3 g/l |
| pH | 2.0 |
| Temperature | 80° C. |

Plating was continued by repeatedly dipping copper articles while the bath was managed by the above-mentioned procedure. Tin-lead alloy films of a fixed thickness consistently deposited on a number of copper articles while the bath maintained stable chemical deposition capability.

The method for determining the concentration of metal ions in an electroless tin-lead alloy plating bath according to the invention permits for satisfactory bath management.

Example 4

Analysis of tin ion

There was prepared an electroless tin plating bath of the following composition where electroless plating was effected on copper articles under the following conditions. On every plating quantity of 10 μm·dm²/liter, an aliquot was sampled from the bath and a sample, designated No. 4, of the following composition was prepared therefrom. The absorbance of the sample was measured by means of a spectrophotometer, determining the quantity of divalent tin ion. Whenever the divalent tin concentration decreased by 0.1 g/l with the progress of plating, the following replenishers (E) and (F) were supplied to the bath in the indicated rates, allowing plating procedures to be repeated.

The results are shown in Table 4. For comparison purposes, the results of atomic absorption spectrometry (AAS) of the same samples are also reported in Table 4.

| Bath composition and conditions | |
| --- | --- |
| Methanesulfonic acid | 90 g/l |
| Tin methanesulfonate | 20 g/l |
| Thiourea | 120 g/l |
| Sodium hypophosphite | 80 g/l |
| Citric acid | 15 g/l |
| Lauryl pyridinium chloride | 5 g/l |
| EDTA | 3 g/l |
| Total volume | 100 liters |
| pH | 2.0 |
| Temperature | 80° C. |
| Test sample No. 4 | |
| Plating solution | 1 ml |
| Thiourea (100 g/l) | 80 ml |
| Aqueous HCl (1 + 1) | 5 ml |

It was diluted with deionized water to 100 ml and absorbance was measured at a wavelength of 370 nm.

| Replenisher (E): 5 ml/liter | |
| --- | --- |
| Tin methanesulfonate | 520 g/l |
| Methanesulfonic acid | 250 g/l |
| Replenisher (F): 5 ml/liter | |
| Thiourea | 120 g/l |
| Sodium hypophosphite | 3 g/l |
| Citric acid | 25 g/l |

TABLE 4

| Plating quantity | Sn analysis by the invention | Analysis by AAS |
| --- | --- | --- |
| 20 μm·dm²/l | 7.70 g/l | 7.75 g/l |
| 40 | 7.65 | 7.60 |
| 60 | 7.70 | 7.75 |
| 80 | 7.75 | 7.80 |
| 100 | 7.70 | 7.75 |
| 120 | 7.65 | 7.75 |
| 140 | 7.70 | 7.75 |
| 160 | 7.65 | 7.70 |

As is evident from Table 4, the analytical values of tin ion according to the method of the invention are substantially coincident with the analytical values by atomic absorption spectrometry. The method of the invention permits for easy and accurate determination of the tin concentration of an electroless tin plating bath. Tin films of a fixed thickness consistently deposited on a number of copper articles while the bath maintained stable chemical deposition capability.

Example 5

Analysis of tin ion

There was prepared a tin electroplating bath of the following composition where electroplating was effected on copper articles under the following conditions. On every plating quantity of 100 μm·dm²/liter, an aliquot was sampled from the bath and a sample, designated No. 5, of the following composition was prepared therefrom. The absorbance of the sample was measured by means of a spectrophotometer, determining the quantity of divalent tin ion. Whenever the divalent tin concentration decreased by a predetermined amount with the progress of plating, a fresh plating solution was replenished to the bath, allowing plating procedures to be repeated On every replenishment, the divalent tin ion concentration was determined by the same analytical procedure as above The results are shown in Table 5. For comparison purposes, the results of atomic absorption spectrometry (AAS) of the same samples are also reported in Table 5.

| Bath composition and conditions | |
| --- | --- |
| Stannous sulfate | 40 g/l |
| Sulfuric acid | 100 g/l |
| Gelatin | 2 g/l |
| Total volume | 100 liters |
| Cathodic current density | 2 A/dm² |
| Temperature | 20° C. |
| Test sample No. 5 | |
| Plating solution | 0.5 ml |
| Thiourea (100 g/l) | 80 ml |
| Aqueous HCl (1 + 1) | 5 ml |

It was diluted with deionized water to 100 ml and absorbance was measured at a wavelength of 370 nm.

TABLE 5

| Plating quantity | Sn analysis by the invention | Analysis by AAS |
| --- | --- | --- |
| 100 μm · dm²/l | 22.0 g/l | 23.0 g/l |
| 200 | 22.0 | 22.5 |
| 300 | 22.5 | 22.5 |
| 400 | 22.5 | 23.0 |
| 500 | 22.5 | 22.5 |
| 600 | 23.0 | 22.5 |
| 700 | 22.5 | 24.0 |
| 800 | 23.0 | 23.5 |

As is evident from Table 5, the analytical values of tin ion according to the method of the invention are substantially coincident with the analytical values by atomic absorption spectrometry. The method of the invention permits for easy and accurate determination of the tin concentration of a tin electroplating bath and satisfactory management thereof.

Example 6

Analysis of lead ion

There was prepared a lead electroplating bath of the following composition where electroplating was effected on articles under the following conditions. On every plating quantity of 100 μm·dm²/liter, an aliquot was sampled from the bath and a sample, designated No. 6, of the following composition was prepared therefrom. The absorbance of the sample was measured by means of a spectrophotometer, determining the quantity of lead ion. Whenever the lead concentration decreased by a predetermined amount with the progress of plating, a fresh plating solution was replenished to the bath, allowing plating procedures to be repeated. On every replenishment, the lead ion concentration was determined by the same analytical procedure as above.

The results are shown in Table 6. For comparison purposes, the results of atomic absorption spectrometry (AAS) of the same samples are also reported in Table 6.

| Bath composition and conditions | |
| --- | --- |
| Lead borofluoride | 180 g/l |
| Fluoroboric acid | 190 g/l |
| Boric acid | 30 g/l |
| Gelatin | 2 g/l |
| Total volume | 100 liters |
| Cathodic current density | 2 A/dm² |
| Temperature | 30° C. |
| Test sample No. 6 | |
| Plating solution | 0.1 ml |
| Thiourea (100 g/l) | 80 ml |
| Aqueous HCl (1 + 1) | 5 ml |

It was diluted with deionized water to 100 ml and absorbance was measured at a wavelength of 370 nm.

TABLE 6

| Plating quantity | Pb analysis by the invention | Analysis by AAS |
| --- | --- | --- |
| 100 μm · dm²/l | 98.0 g/l | 100.5 g/l |
| 200 | 99.0 | 99.5 |
| 300 | 101.0 | 101.0 |
| 400 | 98.0 | 100.5 |
| 500 | 97.0 | 98.0 |
| 600 | 99.5 | 99.0 |
| 700 | 100.5 | 100.0 |
| 800 | 99.0 | 98.0 |

As is evident from Table 6, the analytical values of lead ion according to the method of the invention are substantially coincident with the analytical values by atomic absorption spectrometry. The method of the invention permits for easy and accurate determination of the lead concentration of a lead electroplating bath and satisfactory management thereof.

Example 7

Analysis of lead ion

There was prepared a tin-lead alloy electroplating bath of the following composition where electroplating of tin-lead alloy was effected on copper articles under the following conditions. On every plating quantity of 10 μm·dm²/liter, an aliquot was sampled from the bath and a sample, designated No. 7, of the following composition was prepared therefrom. The sample was measured for absorbance by means of a spectrophotometer, determining the combined absorbance of tin and lead ions. Separately, the concentration of tin ion was determined by iodometric titration and the absorbance of tin ion was calculated therefrom. The combined absorbance minus the tin absorbance gave a net absorbance of lead ion. The concentration of lead ion was calculated from the lead absorbance.

Whenever the lead concentration decreased by a predetermined amount with the progress of plating, a fresh plating solution was replenished to the bath, allowing plating procedures to be repeated On every replenishment, the lead ion concentration was determined by the same analytical procedure as above.

The results are shown in Table 7. For comparison purposes, the results of atomic absorption spectrometry (AAS) of the same samples are also reported in Table 7.

| Bath composition and conditions | |
| --- | --- |
| Stannous borofluoride | 130 g/l |
| Lead borofluoride | 50 g/l |
| Fluoroboric acid | 125 g/l |
| Boric acid | 25 g/l |
| Peptone | 5 g/l |
| Total volume | 100 liters |
| Cathodic current density | 2 A/dm$^2$ |
| Temperature | 25° C. |
| Test sample No. 7 | |
| Plating solution | 0.1 ml |
| Thiourea (100 g/l) | 80 ml |
| Aqueous HCl (1 + 1) | 5 ml |

It was diluted with deionized water to 100 ml and absorbance was measured at a wavelength of 370 nm.

TABLE 7

| Plating quantity | Pb analysis by the invention | Analysis by AAS |
| --- | --- | --- |
| 100 μm · dm$^2$/l | 27.0 g/l | 28.0 g/l |
| 200 | 28.0 | 27.0 |
| 300 | 29.5 | 28.5 |
| 400 | 28.5 | 29.0 |
| 500 | 30.0 | 29.5 |
| 600 | 27.5 | 28.0 |
| 700 | 29.0 | 28.5 |
| 800 | 30.5 | 30.0 |

As is evident from Table 7, the analytical values of lead ion according to the method of the invention are substantially coincident with the analytical values by atomic absorption spectrometry. The method of the invention permits for easy and accurate determination of the lead concentration of a tin-lead alloy electroplating bath and satisfactory management thereof.

Example 8

Analysis of lead ion

There was prepared a lead electroplating bath of the following composition where electroplating of lead was effected on copper articles under the following conditions. On every plating quantity of 100 μm·dm$^2$/liter, an aliquot was sampled from the bath and a sample, designated No. 8, of the following composition was prepared therefrom. The sample was measured for absorbance by means of a spectrophotometer, determining the absorbance of lead ion. Whenever the lead concentration decreased by a predetermined amount with the progress of plating, a fresh plating solution was replenished to the bath, allowing plating procedures to be repeated. On every replenishment, the lead ion concentration was determined by the same analytical procedure as above.

The results are shown in Table 8. For comparison purposes, the results of atomic absorption spectrometry (AAS) of the same samples are also reported in Table 8.

| Bath composition and conditions | |
| --- | --- |
| Lead borofluoride | 180 g/l |
| Fluoroboric acid | 190 g/l |
| Boric acid | 30 g/l |
| Gelatin | 2 g/l |
| Total volume | 100 liters |
| Cathodic current density | 2 A/dm$^2$ |
| Temperature | 30° C. |
| Test sample No. 8 | |
| Plating solution | 0.1 ml |
| Tartaric acid (400 g/l) | 10 ml |
| KI (100 g/l) | 10 ml |

It was diluted with deionized water to 100 ml and absorbance was measured at a wavelength of 340 nm.

TABLE 8

| Plating quantity | Pb analysis by the invention | Analysis by AAS |
| --- | --- | --- |
| 100 μm · dm$^2$/l | 98.0 g/l | 101.0 g/l |
| 200 | 97.0 | 100.5 |
| 300 | 99.5 | 98.0 |
| 400 | 100.5 | 99.0 |
| 500 | 99.0 | 100.0 |
| 600 | 98.0 | 98.0 |
| 700 | 99.0 | 100.5 |
| 800 | 101.0 | 99.5 |

As is evident from Table 8, the analytical values of lead ion according to the method of the invention are substantially coincident with the analytical values by atomic absorption spectrometry. The method of the invention permits for easy and accurate determination of the lead concentration of a lead electroplating bath and satisfactory management thereof.

Example 9

Analysis of lead and tin ions

There was prepared a tin-lead alloy electroplating bath of the following composition where electroplating of tin. lead alloy was effected on copper articles under the following conditions. On every plating quantity of 100 μm·dm$^2$/liter, two aliquots were sampled from the bath and the concentrations of lead ion and divalent tin ion in the bath were determined therefrom by the following procedures (1) and (2). A fresh plating solution was replenished to the bath in accordance with the thus determined concentrations of lead ion and divalent tin ion, allowing plating procedures to be repeated. On every replenishment, the concentrations of lead ion and divalent tin ion were determined by the same analytical procedures as above.

The results are shown in Table 9. For comparison purposes, the results of atomic absorption spectrometry (AAS) of the same samples are also reported in Table 9.

| Bath composition and conditions | |
| --- | --- |
| Stannous borofluoride | 130 g/l |
| Lead borofluoride | 50 g/l |
| Fluoroboric acid | 125 g/l |
| Boric acid | 25 g/l |
| Peptone | 5 g/l |
| Total volume | 100 liters |
| Cathodic current density | 2 A/dm$^2$ |
| Temperature | 25° C. |

(1) Analysis of lead ion

A sample, designated No. 9-1, of the following composition was prepared from one aliquot of the plating solution. The sample was measured for absorbance, from which the concentration of lead ion was determined.

| Test sample No. 9-1 | |
| --- | --- |
| Plating solution | 0.1 ml |
| Tartaric acid (400 g/l) | 10 ml |
| KI (100 g/l) | 10 ml |

It was diluted with deionized water to 100 ml and absorbance was measured at a wavelength of 340 nm.

(2) Analysis of tin ion

A sample, designated No. 9-2, of the following composition was prepared from the other aliquot of the plating solution. The sample was measured for absorbance, obtaining the combined absorbance of lead ion and divalent tin ion. The combined absorbance minus the absorbance of lead ion measured in (1) gave a net absorbance of divalent tin ion, from which the concentration of divalent tin ion was determined.

| Test sample No. 9-2 | |
| --- | --- |
| Plating solution | 0.1 ml |
| Thiourea (100 g/l) | 80 ml |
| Aqueous HCl (1 + 1) | 5 ml |

It was diluted with deionized water to 100 ml and absorbance was measured at a wavelength of 370 nm.

TABLE 9

| Plating quantity | Analysis by Invention | | Analysis by AAS | |
| --- | --- | --- | --- | --- |
| | Pb ion | Sn ion | Pb ion | Sn ion |
| 100 μm · dm²/l | 27.0 g/l | 53.0 g/l | 28.5 g/l | 55.5 g/l |
| 200 | 27.5 | 55.0 | 29.0 | 57.0 |
| 300 | 29.0 | 53.5 | 29.5 | 52.0 |
| 400 | 30.5 | 56.0 | 28.0 | 55.0 |
| 500 | 28.0 | 55.5 | 28.5 | 56.0 |
| 600 | 29.5 | 54.0 | 30.0 | 54.5 |
| 700 | 28.5 | 53.5 | 28.0 | 53.0 |
| 800 | 30.0 | 56.0 | 27.0 | 54.0 |

As is evident from Table 9, the analytical values of lead and tin according to the method of the invention are substantially coincident with the analytical values by atomic absorption spectrometry. The method of the invention permits for easy and accurate determination of the lead and tin ion concentrations of a tin-lead alloy electroplating bath and satisfactory management thereof.

While the invention has been described in what is presently considered to be a preferred embodiment, other variations and modifications will become apparent to those skilled in the art. It is intended, therefore, that the invention not be limited to the illustrative embodiments, but be interpreted within the full spirit and scope of the appended claims.

We claim:

1. A method for analyzing a tin, lead or tin-lead alloy plating solution having copper dissolved therein as a complex with thiourea or its derivative in the plating solution comprising the steps of:

taking a sample from the solution, adding an oxidizing agent to said sample, thereby simultaneously decomposing thiourea or its derivative and oxidizing a monovalent copper ion in the sample to a divalent copper ion, adjusting the pH of said sample to between pH 4 and pH 11, adding a color developing agent to said sample, thereby causing the divalent copper ion to develop its color, and quantitatively determining the concentration of divalent copper ion by colorimetry.

2. The method of claim 1 wherein said color developing agent is selected from the group consisting of ammonia, amines, 2,2'-bipyridyl, 1,10-phenanthroline and phenanthroline derivatives.

3. A method for analyzing a tin, lead or tin-lead alloy plating solution containing at least one divalent metal ion selected from the group consisting of tin and lead ions, comprising the steps of:

taking a sample from the solution, adding thiourea or its derivative to the sample thereby causing the divalent metal ion to develop its color, and quantitatively determining the concentration of the divalent metal ion by colorimetry.

4. A method for analyzing a lead or tin-lead alloy plating solution containing a copper ion in addition to a lead ion, comprising the steps of:

taking a sample from the solution, adding an oxidizing agent to said sample thereby simultaneously decomposing thiourea or its derivative and oxidizing a monovalent copper ion in the sample to a divalent copper ion, adjusting the pH of said sample to between pH 4 and pH 11, adding a color developing agent to said sample thereby causing the divalent copper ion to develop its color, and quantitatively determining the concentration of divalent copper ion by colorimetry taking a second sample from the solution, adding an iodine to said second sample, causing said lead and copper ions to develop their color, quantitatively determining the combined concentration of said lead and copper ions by colorimetry, and subtracting said concentration of copper ion from said combined concentration to provide a quantitative determination of lead ion.

5. A method for analyzing a tin-lead alloy plating solution for quantitative determination of divalent tin ion and lead ion, comprising the steps of:

taking a first sample from the solution, adding an iodide as a color developing agent to said first sample thereby causing said lead ion to develop its color, quantitatively determining the concentration of said lead ion by colorimetry, taking a second sample from the solution, adding thiourea or its derivative to said second sample thereby causing said divalent tin ion and lead ion to develop their color, quantitatively determining the combined concentration of said divalent tin and lead ions by colorimetry, and subtracting said concentration of lead ion from said combined concentration of divalent tin and lead ions to provide the concentration of divalent tin ion.

6. A method for analyzing a tin-lead alloy plating solution containing copper ion for quantitative determination of divalent tin ion and lead ion, the method comprising the steps of:

determining the copper ion concentration of the solution, taking a first sample from the solution, adding an iodide to said first sample thereby causing said lead ion and copper ion to develop their color, quantitatively determining the combined concentration of lead and copper ions by colorimetry, subtracting said concentration of copper ion from said combined concentration of lead and copper ions to provide a quantitative determination of lead ion, taking a second sample from the solution, adding thiourea or its derivative to said second sample thereby causing said divalent tin ion and lead ion to develop their color, quantitatively determining the combined concentration of said divalent tin and lead ions by colorimetry, and subtracting said concentration of lead ion from said combined concentration of divalent tin and lead ions to provide a quantitative determination of divalent tin ion.

7. A method for analyzing an electroless tin-lead alloy plating solution for quantitative determination of copper ion, lead ion, and divalent tin ion, comprising the steps of:

Step 1: taking a first sample from the solution, adding an oxidizing agent to said first sample, thereby converting a monovalent copper ion to a divalent copper ion, and determining the concentration of copper ion by colorimetry, Step 2: taking a second sample from the solution, adding an iodide to said second sample, measuring the absorbance of said second sample to provide a combined absorbance of copper and lead ions, subtracting an absorbance attributable to copper ion as calculated from the concentration of copper ion determined in Step 1 from the combined absorbance to provide an absorbance attributable to only lead ion, and calculating the concentration of lead ion from the absorbance of lead ion, and Step 3: taking a third sample from the solution, adding thiourea or its derivative to said third sample, measuring the absorbance of said third sample to provide a combined absorbance of divalent tin and lead ions, subtracting an absorbance attributable to lead ion s calculated from the concentration of lead ion determined in Step 2 from the combined absorbance to provide an absorbance attributable to only divalent tin ion, and calculating the concentration of divalent tin ion from the absorbance of divalent tin ion.

8. The method of claim 1 further comprising the step of adding a complexing agent capable of forming complexes with Tin (IV) and Lead (II), prior to the colorimetric determination.

9. The method of claim 8, wherein said complexing agent is selected from the group consisting of oxalic acid, tartaric acid, citric acid, EDTA and its salts, and triethanol amine.

10. The method of claim 1, wherein said oxidizing agent is selected from the group consisting of peroxides, persulfates, chlorous acid and chlorites.

11. The method of claim 10, wherein said oxidizing agent is hydrogen peroxide.

12. The method of claim 1, wherein said quantitative colorimetric determination of the concentration of divalent copper ion is performed in the range of wavelengths from 500 to 800 nm.

13. The method of claim 3, wherein said thiourea derivative is selected from the group consisting of dimethylthiourea, diethylthiourea, dimethylolthiourea and diphenylthiourea.

14. The method of claim 3, further comprising the step of adding a reducing agent for converting tetravalent tin ions into divalent tin ions, prior to the addition of thiourea.

15. The method of claim 14 wherein said reducing agent is selected from the group consisting of metallic zinc powder, tetrahydroborates, hydrazine and hydrazine salts.

16. The method of claim 4, wherein said iodide is selected from the group consisting of potassium iodide and sodium iodide.

17. The method of claim 5, wherein said iodide is selected from the group consisting of potassium iodide and sodium iodide.

18. The method of claim 6, wherein said iodide is selected from the group consisting of potassium iodide and sodium iodide.

19. The method of claim 7, wherein said iodide is selected from the group consisting of potassium iodide and sodium iodide.

20. The method of claim 5, wherein said thiourea derivative is selected from the group consisting of dimethylthiourea, diethylthiourea, dimethylolthiourea and diphenylthiourea.

21. The method of claim 6, wherein said thiourea derivative is selected from the group consisting of dimethylthiourea, diethylthiourea, dimethylolthiourea and diphenylthiourea.

22. The method of claim 7, wherein said oxidizing agent is selected from the group consisting of peroxides, persulfates, chlorous acid and chlorites.

23. The method of claim 4, further comprising the step of adding a complexing agent selected from the group consisting of oxalic acid, tartaric acid, citric acid, EDTA, hydroxyphosphoric acid and salts thereof.

24. The method of claim 6, further comprising the step of adding a complexing agent selected from the group consisting of oxalic acid, tartaric acid, citric acid, EDTA, hydroxyphosphoric acid and salts thereof.

25. The method of claim 7, further comprising the step of adding a complexing agent selected from the group consisting of oxalic acid, tartaric acid, citric acid, EDTA, hydroxyphosphoric acid and salts thereof.

* * * * *

UNITED STATES PATENT AND TRADEMARK OFFICE
CERTIFICATE OF CORRECTION

PATENT NO. : 5,294,554
DATED : March 15, 1994
INVENTOR(S) : Patrick S. Gentile et al.

It is certified that error appears in the above-indentified patent and that said Letters Patent is hereby corrected as shown below:

IN THE REFERENCES CITED

On the title page, under "OTHER PUBLICATIONS", column 2, line 7, delete "Genitle" and substitute therefor --Gentile--.

On the title page, under "OTHER PUBLICATIONS", column 2, line 8, delete "Genitle" and substitute therefor --Gentile--.

In column 1, line 41, after "also", delete "." and substitute therefor --,--.

In column 2, line 21, after "CFU-GM", insert --.--.

In column 3, line 23, delete "lipopolysaccharide".

In column 3, line 24, delete "phytohemagglutinin".

In column 3, line 58, after "SDS-PAGE", insert --.--.

In column 5, line 27, after "purified", insert --.--.

UNITED STATES PATENT AND TRADEMARK OFFICE
CERTIFICATE OF CORRECTION

PATENT NO. : 5,294,554
DATED : March 15, 1994
INVENTOR(S) : Patrick S. Gentile et al.

It is certified that error appears in the above-indentified patent and that said Letters Patent is hereby corrected as shown below:

In column 10, line 47, delete "Bm Cm" and substitute therefor --BM CM--.

In column 10, line 54, delete "preciptate" and substitute therefor --precipitate--".

In column 11, line 55, after "Nature,", delete "277" and substitute therefor --227--.

In column 12, line 35, under "Colonies" and after "Control Eluate 7", delete "101" and substitute therefor --110--.

Column 14, claim 1, line 5, delete "from" and substitute therefor --for--.

Signed and Sealed this

Fourth Day of October, 1994

Attest:

BRUCE LEHMAN

Attesting Officer    Commissioner of Patents and Trademarks